United States Patent [19]

Kurokawa et al.

[11] Patent Number: 5,714,181
[45] Date of Patent: Feb. 3, 1998

[54] METHOD FOR REDUCING THE INCIDENCE OF PREMATURE PIGLETS BY USING FEED CONTAINING OLIGOSACCHARIDES

[75] Inventors: Satoru Kurokawa; Kiyoshi Hashimoto; Yasushi Yoshimi, all of Tokyo; Kazuhiko Hirose, Osaka; Takahisa Tokunaga, Tokyo; Toshiaki Kono; Akihiro Kodaira, both of Saitama, all of Japan

[73] Assignee: Meiji Seika Kaisha, Ltd., Tokyo, Japan

[21] Appl. No.: 501,449

[22] Filed: Jul. 12, 1995

[30] Foreign Application Priority Data

Jul. 13, 1994 [JP] Japan ................................ 6-160977

[51] Int. Cl.$^6$ ................................ A23K 1/00; A23K 1/18
[52] U.S. Cl. ................................ 426/2; 426/658; 426/805; 426/807
[58] Field of Search ................................ 426/2, 658, 805, 426/807

[56] References Cited

U.S. PATENT DOCUMENTS

| | | |
|---|---|---|
| 4,788,065 | 11/1988 | Nakamura . |
| 4,873,229 | 10/1989 | Deya et al. ................... 426/805 |

FOREIGN PATENT DOCUMENTS

| | | | |
|---|---|---|---|
| 0133547 | 2/1985 | European Pat. Off. . | |
| 0464362 | 1/1992 | European Pat. Off. . | |
| 56-154967 | 11/1981 | Japan ............... | A23L 1/236 |
| 52-19897 | 8/1993 | Japan . | |

*Primary Examiner*—David L. Lacey
*Assistant Examiner*—Choon P. Koh
*Attorney, Agent, or Firm*—Sughrue, Mion, Zinn, Macpeak & Seas, PLLC

[57] ABSTRACT

The present invention is directed to a convenient and economical method for improving the rate of raising newborn piglets from the pregnancy of the sow to the weaning of the piglets. The method reduces the incidence of premature piglets and increases the lacteal yield of breeding sows by feeding the breeding sows a feed containing saccharides mainly composed of oligosaccharides.

9 Claims, No Drawings

METHOD FOR REDUCING THE INCIDENCE OF PREMATURE PIGLETS BY USING FEED CONTAINING OLIGOSACCHARIDES

FIELD OF THE INVENTION

This invention relates to a method for reducing the incidence of premature piglets and increasing the lacteal yield of breeding sows by feeding the sows with a feed containing saccharides mainly composed of oligosaccharides. This invention aims at elevating the rate of raising newborns.

BACKGROUND OF THE INVENTION

With the recent tendency of Japanese eating habits toward the Western style, the demand for meat has been increasing. Therefore, meat manufacturers need to develop an effective feeding method. On the other hand, the Japanese livestock industry should further improve productivity to compete on the world market.

Productivity might be improved by, for example, enlarging the litter size, elevating the rate of raising infants and increasing the farrowing frequency. Although improvements in livestock breeding and progress in rearing equipment and environmental sanitation have increased the litter size and elevated the rate of raising newborns, these effects are still insufficient. When domestic animals are fed at an increased rearing density, for example, the rearing environment is worsened and the animals frequently suffer from diarrhea, loose stool, etc., thus undergoing incomplete growth. Attempts have also been made to elevate the rearing efficiency by hastening weaning. In such a case, however, it is frequently observed that infants feel serious stress and take a reduced amount of feed, which causes a temporary loss in body weight and a decrease in the rate of raising. Also, early weaning would retard the recurrence of estrus of breeding animals after weaning. Thus it is sometimes observed that such a treatment does not always contribute to the increase in farrowing frequency.

In domestic animals, including pigs, the growth of infants is affected mainly by the birth weight of the newborn and the lacteal yield of breeding animals, in addition to the general factors of, for example, temperature and humidity. In the case of pigs, for example, the mortality rate of newborns with a birth weight of less than 1 kg amounts to 55 to 100%. Such a high mortality rate is caused by the fact that a newborn with a small body weight can hardly maintain its body temperature, has only limited suckling power and is frequently crushed to death by its mother. When the lacteal yield is insufficient, on the other hand, the newborns have poor resistance against diseases and tend to suffer from diseases. In this case, the growth of the newborns until weaning is inhibited as a matter of course.

Accordingly, a method is needed which is to be employed from the pregnancy period to weaning for efficiently reducing the ratio of newborns with small birth weight (i.e., premature piglets) and increasing the lacteal yield during the lactation period without needing large labor or a high cost.

SUMMARY OF THE INVENTION

The present inventors have conducted extensive studies in order to solve the above-mentioned problems. As a result, they have successfully discovered for the first time that a feed containing saccharides mainly composed of oligosaccharides exhibits excellent effects. The present invention has been completed based on this finding.

Accordingly, the present invention aims at elevating the rate of raising newborns by providing a method for reducing the incidence of premature piglets and increasing the lacteal yield of sows by using a feed for breeding sows which contains saccharides mainly composed of oligosaccharides.

DETAILED DESCRIPTION OF THE INVENTION

Examples of the oligosaccharides to be used in the present invention include fructooligosaccharides, galactooligosaccharides, inulooligosaccharides, soybean oligosaccharide, lactulose, isomaltooligosaccharides, lactosucrose and xylooligosaccharide. In particular, oligosaccharides having two or more fructose molecules binding thereto as a constituent, for example, fructooligosaccharides and inulooligosaccharides are preferable therefor.

As an example of the saccharides composed of fructooligosaccharides as the main component, a saccharide composition obtained by treating sucrose with fructose transferase (see JP-A-56-154967, the term "JP-A" as used herein means an "unexamined published Japanese patent application") which is in the form of a mixture of fructooligosaccharides having 1 to 4 fructose molecules binding to sucrose with sucrose, glucose, or fructose, etc. This saccharide composition may be manufactured, for example, by the following method.

BS medium containing 5.0% sucrose, 1.0% peptone, 0.7% bouillon and 0.3% sodium chloride was placed in two test tubes (10 ml each) and sterilized at 120° C. for 30 minutes. One A"ze-ful sample of *Aspergillus niger* (The genus Aspergillus, Williams & Wilkins Corporation, 1965, Item 293) was inoculated to each test tube and incubated at 28° C. for 24 hours. The culture thus obtained was then inoculated to two conical flasks each containing 200 ml of BS medium previously sterilized at 120° C. for 30 minutes (10 ml of culture to each), and subjected to shake culture at 28° C. for 24 hours, giving a master culture.

Twenty liters of BS medium was charged in a 30-liter jar fermentor, sterilized at 120° C. for 30 minutes and, cooled. The master culture prepared above (a total of 400 ml) was inoculated to this medium, and cultivated at 28° C. for 72 hours with aeration and agitation (300 rpm). At the end of cultivation, microbial cells were filtered off, and 20 liters of the filtrate was concentrated and purified by ultrafiltration, giving 2 liters of an enzyme solution (enzyme activity: 240 unit/ml).

Separately, 10 kg of sucrose was dissolved in 6.7 liters of water, and the pH of the resulting solution was adjusted to 5.0. To this solution was added the enzyme solution prepared above in an amount of 48 units per gram of sucrose and the mixture was held at 50° C. for 48 hours to complete transformation. At the end of reaction, the mixture was heated at 100° C. for 15 minutes to deactivate the enzyme, and decolorized by addition of activated charcoal (0.5% on solid base). After removal of the charcoal, the filtrate was treated with ion-exchange resins (AMBERLITE IR120B and AMBERLITE IRA411) and then concentrated, affording 12 kg of a sugar composition consisting of 33% glucose (G), 2% fructose (F), 10% sucrose (GF), 25% 1-kestose (GF2), 25% nistose (GF3) and 5% fructosylnistose (GF4).

The feed for breeding sows according to the present invention which contains saccharides composed of fructooligosaccharides as the main component (hereinafter sometimes referred to simply as FO) is obtained by adding the above-mentioned FO to a common feed for sows. From the viewpoints of effects and costs, the effects of the present invention can be sufficiently achieved by adding the FO in an amount of from 0.1 to 2 parts by weight, preferably from 0.2 to 0.6 parts by weight, per 100 parts by weight of the feed, though the content of FO is not particularly restricted. If needed, other nourishing substances such as vitamins and fats may be added to the feed.

To elevate the rate of raising newborns, the incidence of premature piglets with small birth weight must be reduced and the lacteal yield of sows during the lactation period must be increased. Therefore, another aspect of the present invention is providing a method for reducing the incidence of premature piglets with small birth weight and increasing the lacteal yield of sows during the lactation period by feeding breeding sows with the above-mentioned feed throughout a definite period of from pregnancy to weaning. Although an FO-containing feed for fertile pigs is disclosed in U.S. Pat. No. 4,788,065 and JP-B-3-27186 (the term "JP-B" as used herein means an "examined Japanese patent publication"), these inventions are directed to promoting the recurrence of estrus; thus differing from the present invention in the feeding period. Thus, these references are clearly distinguishable from the present invention.

In the method of the present invention, breeding sows are continuously fed with the feed of the present invention generally from 3 weeks before the farrowing to the weaning. The FO intake per animal is controlled to 10 to 20 g/day from 3 weeks before the farrowing to the farrowing and 5 to 20 g/day from the farrowing to the weaning. The dose may be appropriately varied depending on, for example, the obesity of the sows and the season.

With the use of this method, the ratio of premature piglets with birth weights less than 1 kg can be reduced, the average lacteal yield of sows and the body weight gain of piglets can be increased and thus the rate of raising newborns can be elevated.

To further illustrate the present invention, and not by way of limitation, the following examples will be given.

EXAMPLE 1

In order to examine the effects of an FO-containing feed on the lacteal yield of sows and the incidence of premature piglets, a preliminary test for determining the feeding period was performed. Sixteen breeding sows were divided into the following 4 groups each having 4 animals. Then these sows were fed in 3 farms A, B and C.

Test group: a feed additive Oligo SI (manufactured by Meiji Seika Kaisha, Ltd., FO content: about 27%) was given in a dose of 60 g/day/animal during each period as defined below.

(1) From 1 week before the farrowing to the farrowing.

(2) From 2 weeks before the farrowing to the farrowing.

(3) From 3 weeks before the farrowing to the farrowing.

Control group: no addition.

The feed was given in the same amount in all of the groups and the animals were allowed to drink water ad libitum. The following items (1) and (2) were evaluated.

(1) Lacteal yield

In each group, the lactation of the mother pigs at the farrowing time was evaluated in the following items and the tendency of an increase in lacteal yield was determined.

(1) Tension in breasts and condition of nipples.

(2) Emission of milk in artificial milking.

(3) Suckling of piglets.

Animals showing improvement in 2 or more of the above items were referred to as effective (+), those showing an improvement in 1 item were referred to as unknown (±) and those showing no improvement were referred to as ineffective (−).

(2) Incidence of premature piglets

Newborns immediately after the farrowing were weighed and those weighing less than 1 kg were referred to as premature piglets. Thus the incidence of premature piglets was determined and evaluated as follows.

a: 10–20%.

b: 20–30%.

c: more than 30%.

TABLE 1

| | Lacteal yield | | | |
|---|---|---|---|---|
| | Test Lot | | | |
| | 3 Weeks | 2 Weeks | 1 Week | Control |
| Farm A | + | ± | − | − |
| Farm B | + | − | − | − |
| Farm C | + | ± | − | − |

Note:
+: effective.
±: unknown.
−: ineffective.

TABLE 2

| | Incidence of premature piglets | | | |
|---|---|---|---|---|
| | Test Lot | | | |
| | 3 Weeks | 2 Weeks | 1 Week | Control |
| Farm A | b | b | c | c |
| Farm B | b | c | c | c |
| Farm C | a | c | c | c |

Note:
a: 10–20%.
b: 20–30%.
c: more than 30%.

EXAMPLE 2

Eighteen breeding sows were divided into a test group and a control group each having 9 animals. The animals in both lots were fed the same amount with a marketed feed for pigs. To the feed for the test lot was added a feed additive Oligo SI (manufactured by Meiji Seika Kaisha, Ltd., FO content: about 27%) at levels of 60 g/day/animal from 3 weeks before the farrowing to the farrowing and 30 g/day/animal from the farrowing to the weaning (day 28), thus giving the feed according to the present invention. The feed was given in a definite amount while the animals were allowed to drink water ad libitum.

Immediately after the farrowing, newborns were weighed individually. Then each newborn was weighed for 2 hours at intervals of 20 minutes and the amount of milk thus given was referred to as the lacteal yield. Before the measurement, the bodily wastes were wiped off with filter paper. As shown in Table 3, continuous feeding with the feed of the present invention reduced the ratio of premature piglets weighing less than 1 kg. As shown in Table 4, the average body weight gain per piglet 2 hours after farrowing and the average total lacteal yield per breeding sow both increased.

TABLE 3

Distribution of birth body weight

| Group | <1.0 kg | 1.0 kg≦ | Total |
|---|---|---|---|
| Test: | | | |
| Piglet No. | 21 | 82 | 103 |
| Ratio (%) | 20.4 | 79.6 | 100.0 |
| Control: | | | |
| Piglet No. | 28 | 68 | 96 |
| Ratio (%) | 29.2 | 70.8 | 100.0 |

TABLE 4

Average body weight gain per piglet and average total lacteal yield per breeding sow 2 hours after farrowing

| Group | No. of Piglets | Average Birth Weight | Average Body Weight Gain | Average Total Lacteal Yield |
|---|---|---|---|---|
| Test | 103 | 1210.6 | 66.4 | 776.9 |
| Control | 96 | 1262.3 | 55.0 | 566.5 |

According to the present invention, a method for reducing the incidence of premature piglets and increasing the lacteal yield of breeding sows with the use of a feed containing saccharides composed of oligosaccharides as a main component can be conveniently provided at a low cost. Thus, the present invention largely contributes to the improvement in the ratio of raising newborns.

While the invention has been described in detail and with reference to specific examples thereof, it will be apparent to one skilled in the art that various changes and modifications can be made therein without departing from the spirit and scope thereof.

What is claimed is:

1. A method for reducing the incidence of premature piglets which comprises:

feeding a feed for breeding sows to a pregnant sow at least two weeks prior to the farrowing, said feed containing saccharides mainly composed of oligosaccharides wherein the amount of the oligosaccharides is greater than 0.1 but less than or equal to 2 parts by weight per 100 parts by weight of the feed and then continuing the feeding through the time of farrowing and until weaning.

2. The method as set forth in claim 1, wherein said oligosaccharides are fructooligosaccharides.

3. A method for increasing the lacteal yield of breeding sows comprising:

feeding breeding sows a feed comprising saccharides mainly composed of oligosaccharides for a period of time of at least two weeks prior to farrowing until weaning, wherein the amount of the oligosaccharides is greater than 0.1 but less than or equal to 2 parts by weight per 100 parts by weight of the feed.

4. The method as set forth in claim 3, wherein said oligosaccharides are fructooligosaccharides.

5. The method as set forth in claim 3, wherein said period of time is about 3 weeks prior to farrowing until weaning.

6. The method as set forth in claim 1, comprising feeding the feed for breeding sows to the pregnant sow at least three weeks prior to the farrowing.

7. A method for reducing the incidence of premature piglets which comprises:

feeding a feed for breeding sows to pregnant sows at least two weeks prior to the farrowing, said feed containing saccharides mainly composed of oligosaccharides wherein the amount of the oligosaccharides is greater than 0.1 but less than or equal to 2 parts by weight per 100 parts by weight of the feed and then continuing the feeding until two hours after farrowing.

8. A method for increasing the lacteal yield of breeding sows comprising:

feeding breeding sows a feed comprising saccharides mainly composed of oligosaccharides for a period of time of at least two weeks prior to farrowing until two hours after farrowing wherein the amount of the oligosaccharides is greater than 0.1 but less than or equal to 2 parts by weight per 100 parts by weight of the feed.

9. The method according to claim 8, wherein the oligosaccharides are selected from the group consisting of fructooligosaccharides, galactooligosaccharides, inulooligosaccharides, soybean oliogsaccharides, lactulose, isomaltooligosaccharides, lactosucrose and xylooligosaccharide.

* * * * *